US010186161B2

(12) United States Patent
Watterson

(10) Patent No.: US 10,186,161 B2
(45) Date of Patent: Jan. 22, 2019

(54) PROVIDING INTERACTION WITH BROADCASTED MEDIA CONTENT

(71) Applicant: ICON Health & Fitness, Inc., Logan, UT (US)

(72) Inventor: Eric C. Watterson, Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 384 days.

(21) Appl. No.: 14/836,533

(22) Filed: Aug. 26, 2015

(65) Prior Publication Data
US 2016/0059079 A1  Mar. 3, 2016

Related U.S. Application Data

(60) Provisional application No. 62/042,718, filed on Aug. 27, 2014.

(51) Int. Cl.
*G09B 5/02* (2006.01)
*G06F 19/00* (2018.01)
(Continued)

(52) U.S. Cl.
CPC ............... *G09B 5/02* (2013.01); *G06F 19/00* (2013.01); *G06F 19/3481* (2013.01); *G09B 19/0038* (2013.01); *A63B 22/0056* (2013.01); *A63B 22/0064* (2013.01); *A63B 22/0076* (2013.01); *A63B 22/02* (2013.01); *A63B 22/0242* (2013.01); *A63B 22/0605* (2013.01); *A63B 22/0664* (2013.01); *A63B 24/0006* (2013.01); *A63B 24/0062* (2013.01); *A63B 69/18* (2013.01); *A63B 2024/0093* (2013.01); *A63B 2071/0625* (2013.01); *A63B 2220/18* (2013.01); *A63B 2220/30* (2013.01);
(Continued)

(58) Field of Classification Search
CPC ... G09B 5/02; G09B 19/0038; G06F 19/3481; A63B 22/0605; A63B 22/0056; A63B 2220/18; A63B 2220/76; A63B 2220/806; A63B 2220/30; A63B 69/18; A63B 2024/0093; A63B 22/0064; A63B 2230/40; A63B 24/0062; A63B 2230/75; A63B 22/02; A63B 2220/807; A63B 24/0006; A63B 22/0664; A63B 2071/0625; A63B 22/0242; A63B 22/0076; A63B 2225/09
See application file for complete search history.

(56) References Cited

U.S. PATENT DOCUMENTS 5,240,417 A * 8/1993 Smithson ......... A63B 21/00181
348/121
5,277,678 A * 1/1994 Friedebach .......... A63B 21/015
434/253
(Continued)

FOREIGN PATENT DOCUMENTS

WO    2001003777    1/2001

*Primary Examiner* — Sundhara Ganesan
(74) *Attorney, Agent, or Firm* — Ray Quinney & Nebeker

(57) ABSTRACT

Providing interaction with media content includes broadcasting media content to a display device, associating a downloadable fitness program with the media content with synchronization indicators to synchronize the downloadable fitness program with the media content, and controlling an operational parameter of an exercise machine based on physical characteristics of an environment depicted in the media content.

20 Claims, 9 Drawing Sheets

(51) Int. Cl.
*A63B 24/00* (2006.01)
*G09B 19/00* (2006.01)
*A63B 69/18* (2006.01)
*A63B 22/00* (2006.01)
*A63B 22/02* (2006.01)
*A63B 22/06* (2006.01)
*A63B 71/06* (2006.01)

(52) U.S. Cl.
CPC ..... *A63B 2220/76* (2013.01); *A63B 2220/806* (2013.01); *A63B 2220/807* (2013.01); *A63B 2225/09* (2013.01); *A63B 2230/40* (2013.01); *A63B 2230/75* (2013.01)

(56) References Cited

U.S. PATENT DOCUMENTS

| | | | | |
|---|---|---|---|---|
| 5,489,249 | A | 2/1996 | Brewer et al. | |
| 5,591,104 | A * | 1/1997 | Andrus | A61B 5/6887 434/247 |
| 5,941,797 | A * | 8/1999 | Kashiwaguchi | A63F 13/95 434/247 |
| 6,004,243 | A * | 12/1999 | Ewert | A63B 24/00 386/E5.002 |
| 6,033,227 | A * | 3/2000 | Ishige | A63B 69/18 434/247 |
| 6,152,856 | A * | 11/2000 | Studor | A63F 13/803 434/247 |
| 6,712,737 | B1 | 3/2004 | Nusbaum | |
| 6,902,513 | B1 * | 6/2005 | McClure | A63B 24/0006 482/4 |
| 7,022,048 | B1 * | 4/2006 | Fernandez | A63B 71/0622 482/51 |
| 2002/0045519 | A1 * | 4/2002 | Watterson | A63B 21/005 482/54 |
| 2004/0127335 | A1 * | 7/2004 | Watterson | H04L 67/02 482/8 |
| 2005/0233866 | A1 * | 10/2005 | Miyamaru | A63B 22/0605 482/57 |
| 2005/0239601 | A1 * | 10/2005 | Thomas | A63B 24/00 482/1 |
| 2006/0063644 | A1 * | 3/2006 | Yang | A63B 22/0605 482/4 |
| 2006/0122035 | A1 * | 6/2006 | Felix | A63B 22/0023 482/8 |
| 2006/0229163 | A1 * | 10/2006 | Waters | A63F 13/65 482/8 |
| 2008/0102424 | A1 * | 5/2008 | Holljes | A63F 13/53 434/247 |
| 2009/0270227 | A1 * | 10/2009 | Ashby | G06F 19/3481 482/8 |
| 2010/0009809 | A1 * | 1/2010 | Carrington | A63B 71/0622 482/4 |
| 2010/0022354 | A1 * | 1/2010 | Fisher | A63B 22/0605 482/8 |
| 2010/0035726 | A1 * | 2/2010 | Fisher | A63B 24/0084 482/8 |
| 2010/0204013 | A1 * | 8/2010 | Chen | A63B 22/0605 482/5 |
| 2011/0082008 | A1 * | 4/2011 | Cheung | A63B 24/0062 482/8 |
| 2011/0164044 | A1 * | 7/2011 | Huang | A63B 21/004 345/473 |
| 2013/0165195 | A1 * | 6/2013 | Watterson | A63B 71/0616 463/6 |
| 2013/0178337 | A1 * | 7/2013 | Brammer | A63B 71/0622 482/9 |
| 2013/0225369 | A1 * | 8/2013 | Fisbein | A63B 22/00 482/1 |
| 2013/0274069 | A1 * | 10/2013 | Watterson | A63B 24/0087 482/9 |
| 2014/0243156 | A1 * | 8/2014 | Cohen | A63B 71/023 482/51 |
| 2015/0011362 | A1 * | 1/2015 | Oh | A63B 22/0605 482/9 |

* cited by examiner

PROVIDING INTERACTION WITH BROADCASTED MEDIA CONTENT

RELATED APPLICATIONS

This application claims priority to U.S. Patent Application Ser. No. 62/042,718 titled "Providing Interaction with Broadcasted Media Content" and filed on 27 Aug. 2014, which application is herein incorporated by reference for all that it discloses.

BACKGROUND

Often exercise enthusiasts work out indoors on a treadmill, stationary bike, elliptical, or another type of exercise machine that have preprogrammed workouts. These preprogrammed workouts may vary the resistance, incline, speed, or other parameters of the exercise machine. The preprogrammed workouts may be installed in the exercise machines from the manufacturers. In other situations, the fitness program is downloadable over the internet. Some of these preprogrammed workouts may be synchronized with video images that display real world routes from remote locations. The programs allow the user to view the same scenery as though the user were actually at the remote location while working out. These preprogrammed work outs may be available from www.iFit.com, which is administered by Icon Health and Fitness, Inc. located in Logan, Utah.

One type of system that coordinates video input with preprogrammed workouts is disclosed in WIPO Patent Application WO/2001/003777 issued to Scott R. Watterson. In this reference, systems and methods provide exercise devices with motivational programming that is particularly well suited for exercise devices that utilize one or more motors, and/or other electrically driven actuators to control one or more operating parameters of the exercise device. Such systems and methods contemplate the use of programming that includes motivational content, and one or more control signals synchronized with the motivational content for controlling the operation of the exercise device. The motivational content preferably includes audio and/or video designed to simulate a group exercise setting. In addition, the motivational content can include instructional and educational content for the benefit of the user. The programming can be live or prerecorded, can be broadcast over available broadcast channels, cable, satellite, the internet or any other means suitable for transmitting audio and/or video signals. The present invention also includes means for reproducing the programming, including the motivational content along with the synchronized control signals.

SUMMARY

In one embodiment, a method for providing interaction with media content includes broadcasting media content to a display device, associating a downloadable fitness program with the media content with synchronization indicators to synchronize the downloadable fitness program with the media content, and controlling an operational parameter of an exercise machine based on physical characteristics of an environment depicted in the media content.

The media content may depict a real time event.

The method may include receiving data about exercise parameters of a user on an exercise machine.

The method may include causing at least one of the exercise parameters to be displayed with the media content in the display device.

The method may include comparing multiple users based at least in part on the exercise parameters in the media content.

The method may include comparing the user with an individual in the media content based at least in part on the exercise parameters by displaying a comparison in the media content.

The downloadable fitness program may include an instruction set to adjust a resistance of an exercise machine, adjust an incline of the exercise machine, adjust a speed of the exercise machine, or combinations thereof.

The media content may be a scheduled program.

Broadcasting media content to the display device may include streaming the media content to the display device.

The media content may be a documentary.

The media content may be a fictional film.

Associating the downloadable fitness program to the media content with the synchronization indicators to synchronize the downloadable fitness program with the media content may include broadcasting the synchronization indicators with the media content.

In one embodiment, a system for providing interaction with media content includes a memory and process. The memory includes program instructions that cause the processor to broadcast media content to a display device, attach a fitness program to the media content that controls at least one operational parameter of an exercise machine based on a physical characteristic of an environment depicted in the media content, and synchronize the fitness program with the media content.

The programmed instructions may cause the processor to receive at least one exercise parameter of a user.

The programmed instructions may cause the processor to compare a user with an individual depicted in the media content and display a comparison in the display device with the media content.

The media content may depict a real time event.

The media content may be a scheduled program.

The programmed instructions may cause the processor to synchronize the fitness program with the media content by providing multiple synchronization indicators with the media content.

In one embodiment, an exercise machine includes a receiver to receive a signal indicating an existence of a downloadable fitness program where the downloadable fitness program being synchronized with media content presented in a display device. The exercise machine also includes an input mechanism to receive input to download the downloadable fitness program and a processor to execute the downloadable fitness program while the media content is presented in the display device. The fitness program includes an instruction set that changes at least one operational parameter of an exercise machine based on a physical characteristic of an environment depicted in the media content.

The media content may include a real time event.

The receiver may receive, from the display device, the signal indicating the existence of the downloadable fitness program.

The receiver may receive, from a source of the media content, the signal indicating the existence of the downloadable fitness program.

The receiver may receive, from a source of the downloadable fitness program, the signal indicating the existence of the downloadable fitness program.

The processor may execute operating instructions of the downloadable fitness program to control a speed of a moveable element of the exercise machine.

The processor may execute operating instructions of the downloadable fitness program to control an incline of the exercise machine.

The processor may execute operating instructions of the downloadable fitness program to control a resistance of a moveable element of the exercise machine.

The exercise machine may include a transmitter to transmit parameters of a workout to a third party.

The media content may be streamed to the display device.

In one embodiment, a display device includes a transmitter to send a signal indicating an existence of a downloadable fitness program where the downloadable fitness program is synchronized with broadcasted media content presented in a screen of the display device. The fitness program may include an instruction set to control at least one operational parameter of an exercise machine based on a physical characteristic of an environment depicted in the media content.

In one embodiment, a method for causing interaction between media content presented in a display device and an exercise machine includes sending a signal indicating an existence of a downloadable fitness program synchronized with media content presented in the display device and sending the downloadable fitness program to the exercise machine where the fitness program includes an instruction set to change at least one operational parameter of an exercise machine based on a physical characteristic of an environment depicted in the media content.

Sending the downloadable fitness program to the exercise machine may occur in response to a request to download the downloadable fitness program.

The media content may depict a real time event.

The method may receive data about exercise parameters of a user on the exercise machine.

The method may cause at least one of the exercise parameters to be displayed with the media content in the display device.

The method may send synchronization indicators based on the media content to the exercise machine, the synchronization indicators synchronize the downloadable fitness program with the media content.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Figure 1:
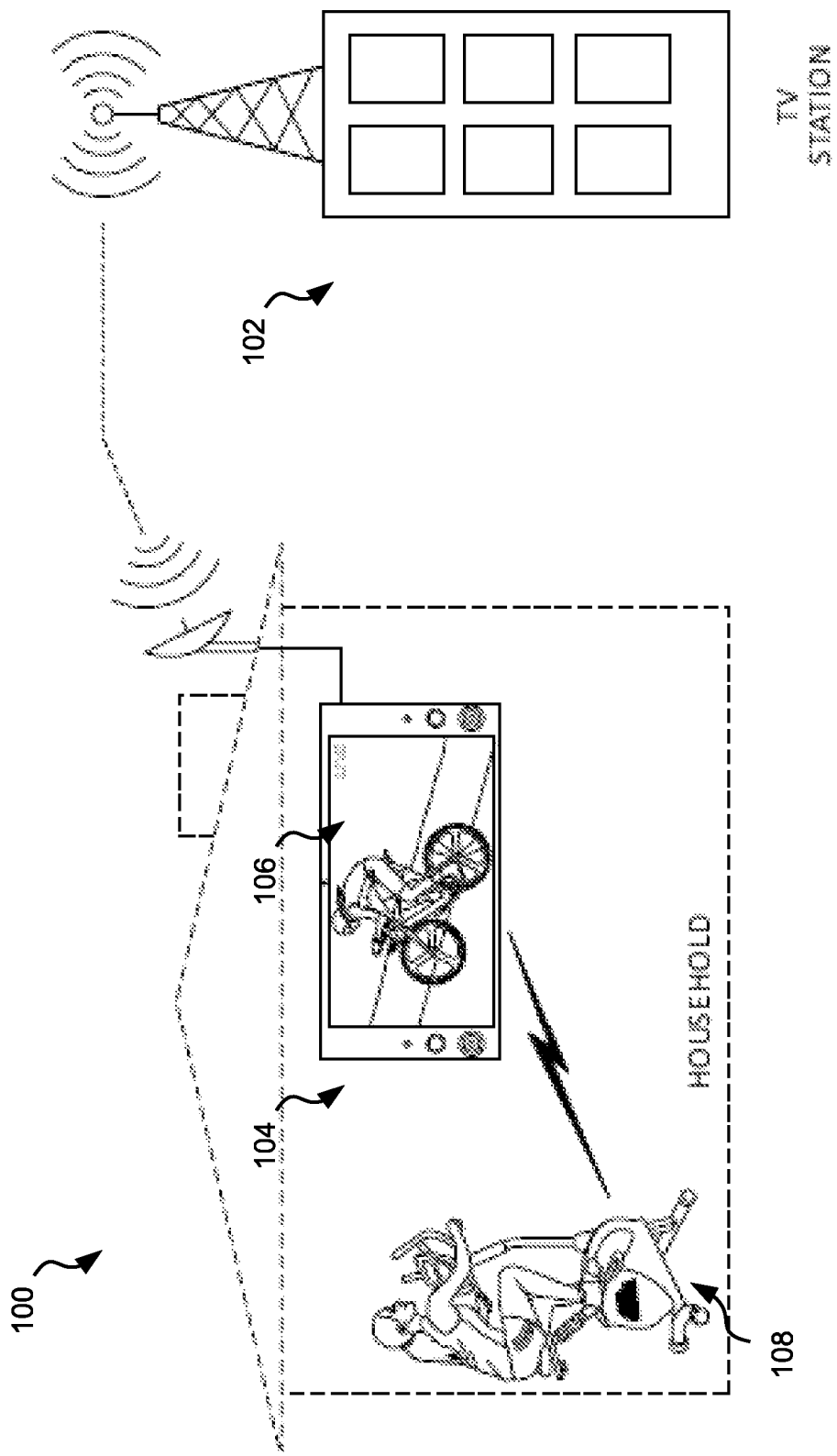
FIG. 1 illustrates a perspective view of an example of a system for interacting with media content in accordance with the present disclosure.

Particularly, with reference to the figures, FIG. 1 depicts a system 100 for interacting with media content in accordance with the present disclosure. In this example, a television station 102 is broadcasting media content to a display device 104, such as a television, a personal computer, or another type of display device. The display device 104 includes a display screen 106 capable of displaying the media content from the television station.

The television station 102 may be in communication with the display device 104 through any appropriate delivery mechanism. For example, the television station may stream live data of an event as the media content to the display device. These delivery mechanisms may be accomplished over a telecommunications network, a radio network, a television network, a local area network, a wide area network, the internet, another type of network, or combinations thereof. Further, any appropriate type of communication protocol may be used. For example, the media content may be sent through a HTTP Live Streaming protocol, Wi-Fi, Bluetooth, media streaming communications protocol, adaptive bitrate streaming, other types of protocols, or combinations thereof. The media content may be movies, scheduled programs, televised programs, live events, commercials, other types of media content, or combinations thereof.

While this example is described with reference to a television station being the source of the media content, any appropriate media content source may be used in accordance with the principles described herein. For example, the media content may be delivered from a movie repository, a sitcom repository, a repository of education programs, or other types of media content accessible over the internet or another type of network. For example, the media content may be accessible through social media sites, libraries of downloadable online videos clips, other locations, or combinations thereof. In some cases, the media content depicts a live event, such as a golfing tournament, a cycling competition, a fashion show, a press release, another type of live event, or combinations thereof. In other examples, the media content is a pre-recorded program capable of being broadcast at a scheduled time or accessible over the internet or another type of network on demand.

Any appropriate type of display device 104 may be used. For example, the display device 104 may include a smart phone, an electronic tablet, a mobile device, a laptop, a desktop, a television, a flat screen, a plasma television, a touch screen, a projector, another type of television, another type of display device, or combinations thereof.

The media content may include multiple components. For example, the media content may include a video component that includes, for example, a motion picture. Further, the media content may include an audio component. This audio component may include the sound recordings associated with the media content such as the voices of the characters in a program. In some examples, the audio component may include music played during this program. Further, the media content may include other types of components.

The media content may be presented to the user through the display device 104. The video component may be presented through the display screen 106, while the audio component may be presented to the user through speakers incorporated into or in communication with the display device 104.

In the illustrated example, the media content includes footage of a real time event being streamed to the display device 104 of a cycling race. Footage of a cyclist 200 is being displayed in the media content. This real time event may be broadcasted live from the location where the race is taking place. This media content provided to the viewing audience may be media content because the competitors of the race may be focused on achieving their best times in the race so that they are not focused on interacting with audiences through available multimedia channels.

While this example has been described with reference to a live cycling race, the principles described above may be applied to other types of media content. For example, this media content may include fictional content where the actors pretend that they are in real world situations that do not have an audience watching or at least do not interact much with this audience. In other examples, the media content may include a documentary where information is directly given to the audience, but the audience is not expected to follow instructions based on the information provided through the documentary content.

The television station or other media content source may send a signal with a message to the display device, which is relayed to an exercise machine 108. This message may indicate that a fitness program is associated with the media content which can be downloaded to the exercise machine 108. This exercise machine 108 may be a treadmill, an elliptical trainer, a stationary bike, a stepper machine, a rowing machine, a skiing machine, another type of exercise machine 108, or combinations thereof. While this example describes the message coming from the television station, the message may come from any appropriate source. For example, a third party may send the message to the display device. In some situations, the message is not sent to the display device, but is sent directly the exercise machine 108. In other examples, the message is sent to the exercise machine 108 indirectly through a device networked with the exercise machine 108. Further, the message may be displayed in the display device without initially communicating with the exercise machine 108. In these circumstances, the user may respond to the message by causing his or her exercise machine 108 to download the fitness program.

The fitness program may be accessible for download over the internet. In other examples, the fitness program can be caused to operate on the exercise machine 108 directly from signals transmitted with the media content.

The fitness program may include an instruction set that can execute a processor to control different parameters of the exercise machine 108. For example, the parameters may include a resistance, an incline angle, a side to side tilt angle, a speed, another operation parameter, or combinations thereof. The fitness program may be synchronized with the media content so that the operating parameters of the exercise machine 108 are coordinated with the events in the media content. For example, if a cyclist in the media content is cycling uphill at an incline angle of three degrees, the fitness program causes the exercise machine 108 to orient the user at the same incline angle. In other examples, if the user is traveling uphill, the fitness program can causes the exercise machine 108 to increase its resistance to more accurately reflect the difficulty of ascending the slope.

In some circumstances, personal information is used to determine the appropriate amount of resistance to apply to the exercise machine 108. For example, the user's weight may be a factor to determine how hard it may be for him or her to ascend an incline depicted in the media content. In other examples, the user's weight may also be used to determine how gravity acts on the user during a downhill portion of a route depicted in the media content. In another example, the user's height and body shape may also be used to determine the appropriate amount of resistance to apply during uphill and downhill portions of the simulated route based on the amount of wind resistance that the user's height and/or shape would cause if the user were actually cycling in the environment of the cyclist depicted in the media content. This wind resistance may be used to determine whether a resistance increase or decrease to the exercise machine is to be made. In some examples, actual wind speed depicted in the media content or actually occurring at the location of a live event depicted in the media content can be used as a factor for determining the amount of resistance to account for the wind resistance. These wind conditions may be collected from a weather station, an onsite sensor, a website, another source, or combinations thereof.

The changes to the exercise machine 108 may mimic a route depicted in the media content. This route may be a racing route, a journey of a character in fictional content, the subject of a documentary, another type of depicted route, or combinations thereof.

In one example, the media content may be a documentary about a journey taken by travelers over a mountain. As the documentary recounts the steps taken by the travelers, the steepness of the mountain side may be depicted in the media content. In some cases, the degree of steepness relative to horizontal is described as a physical characteristic of the environment depicted in the documentary. To be synchronized with the description of the presentation of the physical characteristic, the incline angle of the exercise machine 108 may be changed to reflect the incline of the mountain's steepness relative to horizontal. In another example, the documentary may explain how fast a bear or another type of animal can run. The fitness program may cause the exercise machine 108 to operate at the described speed to give the user an idea of how fast this animal can actually travel.

While the above examples have been described with specific reference to the fitness program being provided by the source of the media content, such as a television station, the fitness program may be provided by any appropriate source. For example, a third party may create the fitness program on the media content provided by another party. The third party can cause the fitness program to be synchronized with the media content. This third party may send the signal to the exercise machine 108 and the user may obtain the fitness program from the third party, such as over the internet or from the signal broadcasted by the third party.

In some examples, the media content sends a synchronization signal at consistent intervals. These signals can be detected by the exercise machine 108 or another device in communication with the exercise machine 108. The fitness program may use the synchronization indicator to determine the pace at which the fitness program can operate to stay synchronized with the media content. In some examples, the fitness program can speed up or slow down the execution of the fitness program to synchronize with the media content. In other examples, the media content is accompanied with commands to change operating parameters as circumstances change in the media content. For example, if the route depicted in the media content changes an angle, the source of the media content may send a single to change the incline angle of the exercise machine 108 to stay synchronized with the depicted route.

In situations where the media content is a scheduled program, the fitness program may also be scheduled. In some circumstances, the user can view beforehand the types of fitness programs that are provided with the different scheduled programs. If the user begins to execute the fitness program at the same time that the media content begins, the user may participate in the entire fitness program provided that the user does not quit before the fitness program concludes at the end of the media content's scheduled showing. In other circumstances, the user may begin the fitness program after the media content started. In this circumstance, the fitness program may cause the exercise machine 108 to operate at a later time point in the program. For example, if the media content started five minutes earlier than when the user begins to execute the fitness program, the user may miss the first five minutes of the fitness program.

In some examples, the media content may be recorded, such as recording the media content with a DVR or another type of magnetic or electronic medium. In these circumstances, the fitness program may be recorded with the media content. Thus, if the user desires to execute the fitness program at a time after the media content's broadcast is concluded, the user may play the media content's recording. This recording may include the synchronization indicators for synchronizing the fitness program with the media content.

In some cases, multiple fitness programs are provided for different types of exercise machines 108. For example, a first user may execute the fitness program with a treadmill while a second user executes the fitness program with a stationary bike. In some circumstances, operating parameters of the different exercise machines are adjusted accordingly. For example, the treadmill may be caused to operate at a speed less than the speed at which cyclists are racing. Similarly, the speeds of a footrace may be increased to for a user participating in the fitness program on a stationary bike. In some examples, the fitness programs for each of the different types of exercise machines is broadcasted over the television network and the exercise machine uses just those versions of the fitness program that is appropriate for the exercise machine's type. In other examples, the user can download the appropriate fitness program version from the remote source, such as a cloud based device or another source across the internet. In this example, the fitness programs may be downloaded to the exercise machines, and a synchronization indicator may be broadcasted by the media content's source. In some examples, the synchronization indicator may be used uniformly for each version of the fitness program regardless of the exercise machine type.

Figure 2:
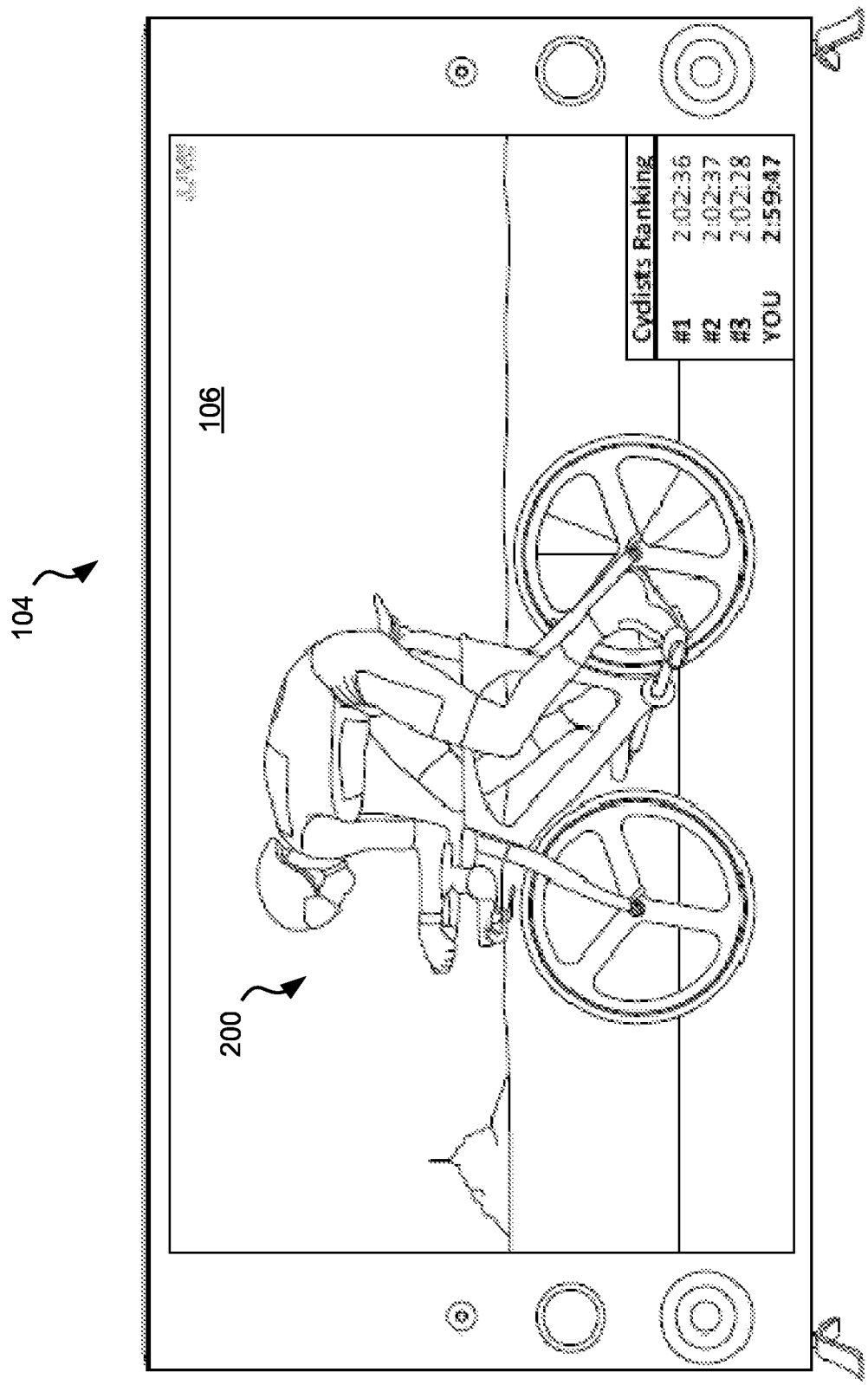
FIG. 2 illustrates a perspective view of an example of a display device in accordance with the present disclosure.

FIG. 2 illustrates a perspective view of an example of a display device 104 in accordance with the present disclosure. In this example, the exercise machine 108 sends the parameters of the exercise machine 108 to the media content source, a third party, the display device, another destination, or combinations thereof. These parameters may reflect the speed at which the user is going, a physiological condition of the user, a distance traveled by the user, another parameter, or combinations thereof.

Such information may be used to compare the user with other users who are also using the fitness program. For example, the user may be using the fitness program while watching a cycling race and may have traveled a certain distance within a predetermined amount of time. This distance may be compared with the distances of others using the fitness program of those depicted in the media content within the same time frame. In other examples, the time is measured for how long it takes for the user to achieve a certain milestone, such as reaching a predetermined checkpoint. The times of the different users and/or the cyclists depicted in the media content may be depicted on the display screen. In some cases, at least one aspect of the user is depicted in the display screen 106. For example, the user's time may be compared to the top cyclist's in the media content by showing the cyclist's times with the user's time.

In other cases, each of the users participating in the fitness program may have at least one aspect of their workout depicted in the media content. For example, the times and associated rankings of the users may be displayed in the media content. Thus, the performance of others may be depicted in the display screen of the user. In circumstances where many users are participating in the fitness program at the same time, the top performers may be depicted. The users participating in the fitness program may compete with each other to reach one of the top spots for being displayed in the media content. In some cases, the user's times are depicted next to the actual athletes participating in the cycling race. In this circumstance, the user's performance is compared to that of the athletes depicted in the media content.

Figure 3:
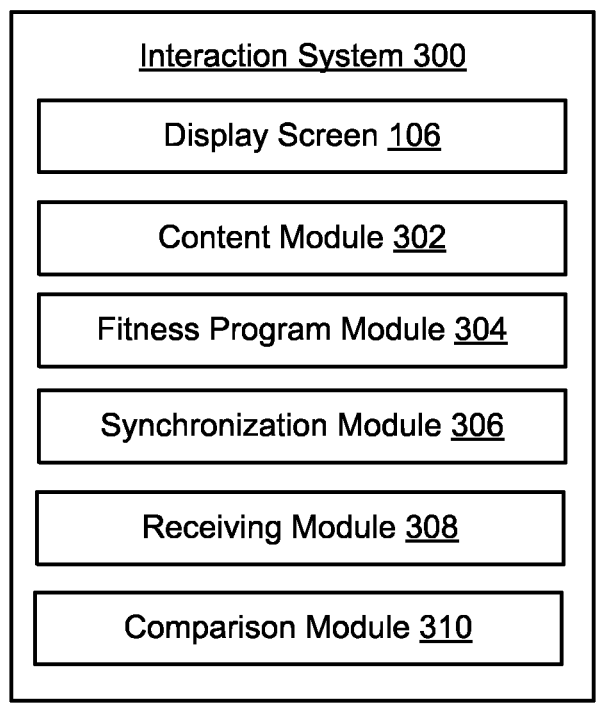
FIG. 3 illustrates a block diagram of an example of a system for interacting with media content in accordance with the present disclosure.

FIG. 3 illustrates a block diagram of an example of a system 300 for interacting with media content in accordance with the present disclosure. In this example, the system 300 includes a display screen 106, a content module 302, a fitness program module 304, a synchronization module 306, a receiving module 308, and a comparison module 310. As used herein, the term "module" includes a combination of hardware and programmed instructions that are necessary for performing the designated function of the module. Components of the modules may be located on the same physical device or some of the components may be located at remote locations that are in communication with the other components of the module.

The content module 302 may include any appropriate mechanism for delivering media content to the display device 104. In some examples, the media content is delivered through a streaming mechanism. In some examples, the media content includes a portion of a television series, a television special, a movie, a sitcom, an education program, a live event, a short video clip, another type of media content, or combinations thereof. The media content may be spectator content.

The fitness program module 304 may include any appropriate instruction set that may be used to control the exercise machine 108. This instruction set may be downloaded from an online source, sent from the media content source, sent from a third party, or available from another mechanism. The fitness program may be configured to operate any appropriate type of exercise machine 108, such as a treadmill, an elliptical trainer, a stationary bike, a stepper machine, a skiing machine, a rowing machine, another type of machine, or combinations thereof. The fitness program may control the exercise machine's incline, resistance, speed, side to side tilt, height, other parameters of the exercise machine 108, or combinations thereof.

In some aspects of the invention, the fitness program module includes an instruction set that causes at least one operational parameter of the exercise machine to change based on at least one physical characteristic of a physical environment depicted in the media content. For example, if the slope of a road or race track changes relative to horizontal, the incline of the exercise machine may also change.

The synchronization module 306 may include any appropriate mechanism for syncing the fitness program with the media content. In some situations, the exercise machine 108 is caused to change parameters in response to different conditions being depicted in the media content. For example, as the slope of the route depicted in the media content changes, so may the incline of the exercise machine 108. In other examples, the media content may depict a route that competitors in the media content are using, and the fitness program may cause the exercise machine 108 to mimic the route based on the user's performance and not necessarily the performance of the competitors. In this situation, the user may not be synced with the competitors, but the user may be synced with a map of the route.

In some cases, synchronization indicators may be sent from the source of the media content, the source of the fitness program, another source, or combinations thereof. In these circumstances, the synchronization indicators provide details about where the fitness program should be based on the media content. For example, the synchronization indicators may be sent at periodic intervals, which enables the fitness program to determine the pace at which it should control the exercise machine 108. In other examples, the synchronization indicators may be sent from the media content to indicate when a change to the exercise machine's operating parameters should be made. For example, when the media content depicts weather changes to a competitor depicted in the media content, such as a gust of wind, the media content source may send a synchronization indicator to indicate a new resistance level at which the exercise machine 108 should be set for synchronizing the experience of the competitor in the media content with the experience of the user.

The receiving module 308 may include any appropriate mechanism for receiving input from the exercise machines. For example, the receiving module 308 may be capable of receiving a signal from the exercise machine that conveys at least one parameter of the user's workout. In some examples, the parameters of the workout that may be sent to the receiving module 308 include a distance, a time taken to achieve a milestone, a physiological parameter, another condition, or combinations thereof.

The comparison module 310 may include any appropriate mechanism for comparing the parameters of the user's workout with exercise parameters of other users, individuals depicted in the media content, animals or machines depicted in the media content, or combinations thereof. For example, the time that a user takes to virtually reach a certain checkpoint in a race course may be compared to the actual time that it took the cyclists depicted in the media content. In this example, the times of selected cyclists may appear in the display screen and the times of the user may appear next to their displayed times. By having the cyclists' times displayed next to the user's time, the user can compare his performance against the cyclists. In other examples, the user's time may be displayed adjacent to other users also using the fitness program. In other examples, the speed of an animal depicted in the media content may be displayed next to the user's speed for comparison.

Figure 4:
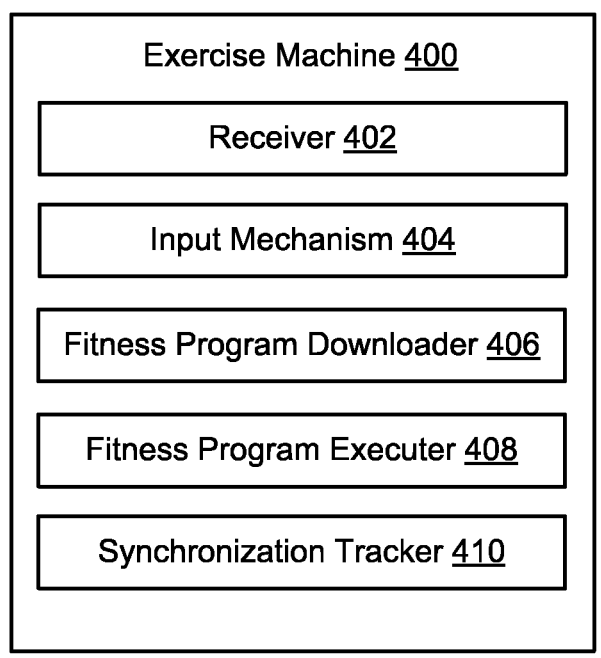
FIG. 4 illustrates a block diagram of an example of an exercise machine in accordance with the present disclosure.

FIG. 4 illustrates a block diagram of an example of the exercise machine 400 in accordance with the present disclosure. In this example, the exercise machine 400 includes a receiver 402, an input mechanism 404, a fitness program downloader 406, a fitness program executer 408, and a synchronization tracker 410.

The receiver 402 may include any appropriate mechanism to receive an appropriate signal indicating that a fitness program is associated with the media content. In some examples, the receiver 402 receives the signal from the television displaying the media content, the source of the media content, a source of a fitness program, a third party, another source, or combinations thereof.

The input mechanism 404 may include any appropriate mechanism for the user to select an option to obtain and/or retrieve the fitness program. In some situations, the receiver 402 may cause a message to be displayed in a console of the exercise machine or otherwise communicate the message to the user that a fitness program is available. In this situation, the user may use the input mechanism to select an option to download the fitness program with the fitness program downloader 406. In some examples, the user can use the input mechanism to select an appropriate version of the fitness program, such as a fitness program specific for a treadmill. In other examples, the exercise machine 400 automatically determines the appropriate version of the fitness program based on the exercise machine's type. In yet other examples, the fitness program is written in this format that allows the fitness program to be executed on multiple types of exercise machines. For example, a single fitness program may be executable on various kinds of treadmills, elliptical trainers, and stationary bikes.

The fitness program executer 408 may include any appropriate type of mechanism to execute the fitness program. This executer 408 may be in communication with actuators that move the exercise platform, change the machine's resistance, change the machine's height, change the machine's side to side tilt, change a motor speed, change another parameter of the exercise machine, or combinations thereof.

The synchronization tracker 410 may include any appropriate type of mechanism to synchronize the fitness program with the media content. For example, the synchronization tracker 410 may receive periodic signals associated with the media content that the synchronization tracker 410 can use to establish a pace of the exercise machine. In other examples, the synchronization tracker 410 can receive inputs from the media content source or other source as to when to make certain changes. In this example, the synchronization tracker 410 may rely on signals from the media content source or other source to make all changes to the exercise machine. But, in other examples the synchronization tracker 410 may rely on these signals to make some changes while relying on other indicators downloaded in the fitness program.

Figure 5:
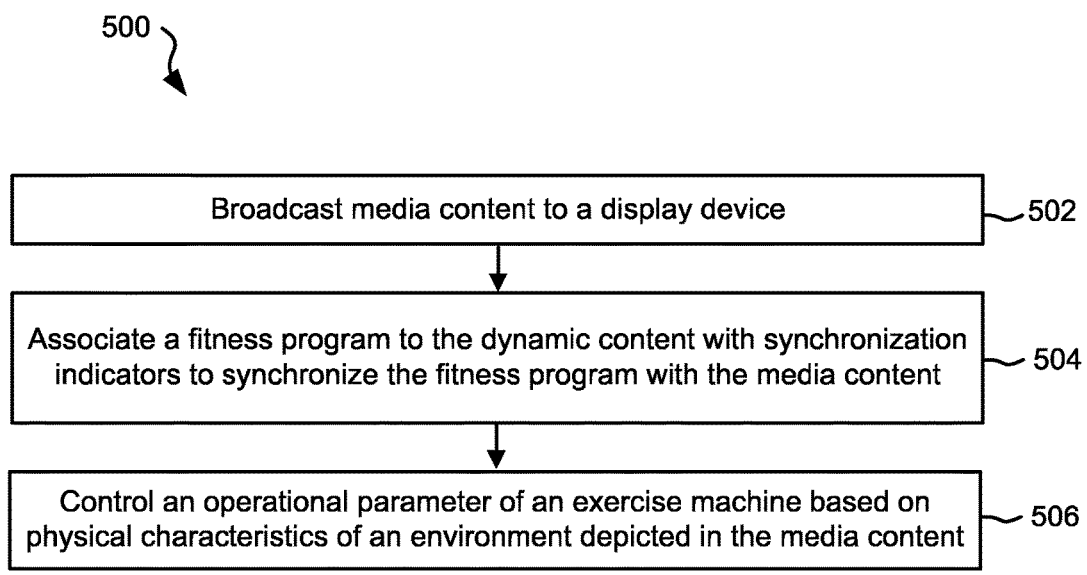
FIG. 5 illustrates a block diagram of an example of a method for providing interaction with broadcasted content in accordance with the present disclosure.

FIG. 5 is a flow diagram illustrating one embodiment of a method 500 for providing interaction with broadcasted content. In this example, the method 500 includes broadcasting 502 media content to a display, associating 504 a fitness program to the media content with synchronization indicators to synchronize the fitness program with the media content, and controlling 506 an operational parameter of an exercise machine based on physical characteristics of an environment depicted in the media content. This method 500 may be implemented with a system 100, 300 in FIGS. 1 and/or 3. In other examples, method 500 may be performed generally by the environment shown in FIG. 1.

At block 502, media content is broadcasted to a display device. This media content may include live events, streamed content, fictional content, documentary content, other types of content, or combinations thereof. In an example, the media content is broadcasted from a television station/network. The display device may be a television, a computer screen, a laptop, a mobile device, a phone, an electronic tablet, another type of display device, or combinations thereof.

At block 504, a fitness program is associated with the media content. This fitness program may be sent at the same time as the media content. In other examples, the fitness program is available for download over the internet or another type of network. The media content may include synchronization indicators that synchronize the fitness program with the media content.

At block 506, at least one operational parameter of an exercise machine based on a physical characteristic of an environment is depicted in the media content. For example, the resistance, incline, speed, height, side to side tilt, or another operational parameter of the exercise machine may change as a physical characteristic in the environment depicted in the media content changes. For example, if a cyclist depicted in the media content is depicted as starting to bike through a sandy portion of a trail, the resistance on an exercise bike may increase in reflect the additional resistance that would be experienced by a user in the depicted environment. Accordingly, the resistance on the exercise bike may be reduced when the cyclist exits the sandy portion of the trail.

Figure 6:
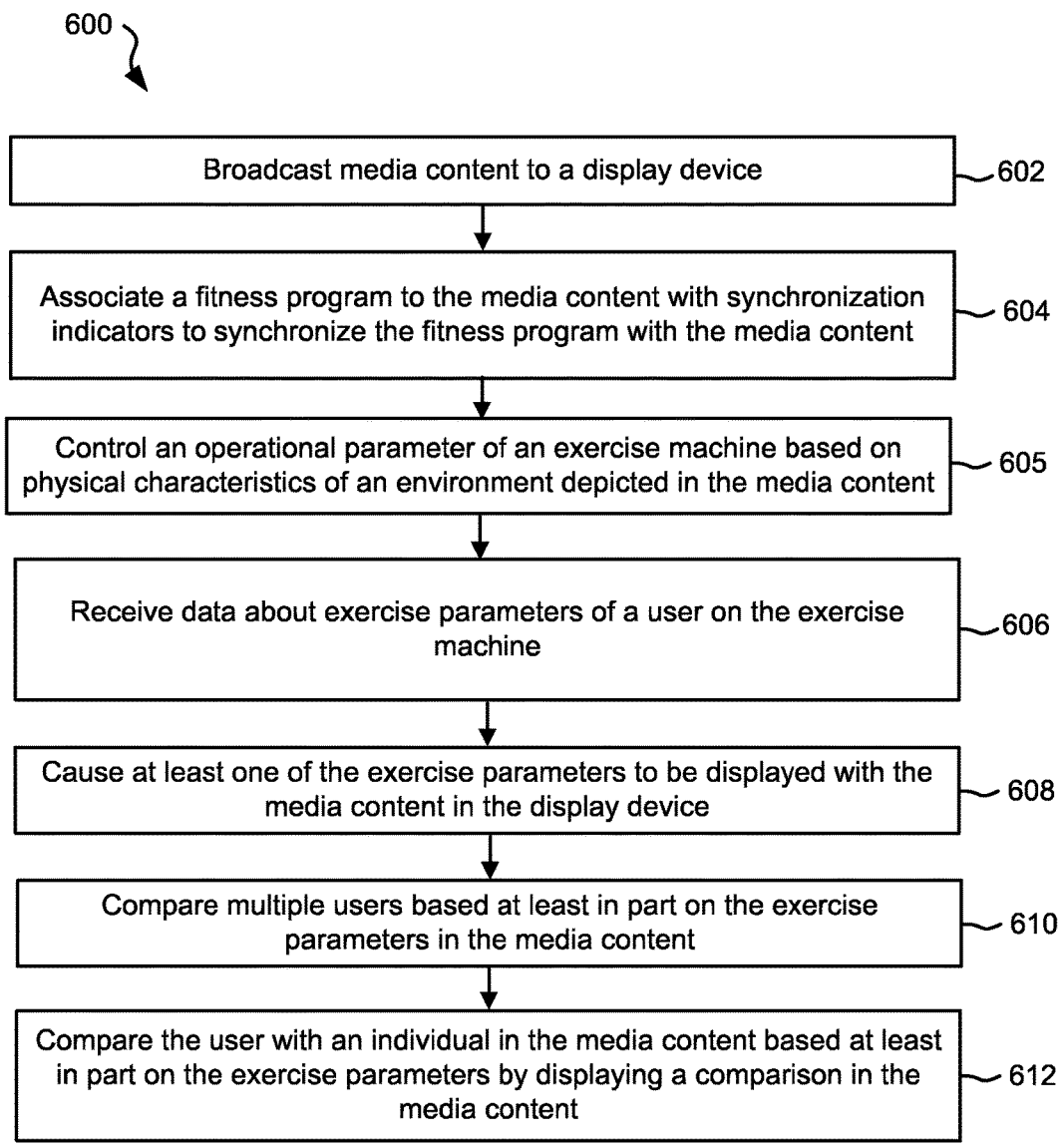
FIG. 6 illustrates a block diagram of an example of a method for providing interaction with broadcasted content in accordance with the present disclosure.

FIG. 6 is a flow diagram illustrating one embodiment of a method 600 for providing interaction with broadcasted content. In this example, the method 600 includes broadcasting 602 media content to a display, associating 604 a fitness program to the media content with synchronization indicators to synchronize the fitness program with the media content, control 605 an operational parameter of an exercise machine based on physical characteristics of an environment depicted in the media content, receive 606 data about exercise parameters of a user on the exercise machine, cause 608 at least one of the exercise parameters to be displayed with the media content in the display device, and compare 610 multiple users based at least in part on the exercise parameters in the media content. This method 600 may be implemented with a system 100, 300 in FIGS. 1 and/or 3. In other examples, method 600 may be performed generally by the environment shown in FIG. 1.

At block 606, data about the exercise parameters of a user on an exercise machine is received. This data may include an incline, a resistance, a speed, a physiological condition, another exercise parameter or combinations thereof. The data may be collected by a sensor incorporated into the exercise machine. In other examples, this data is collected by sensors carried or worn by the user.

At block 608, at least one of the exercise parameters is caused to be displayed with the media content in the display device. For example, the user's speed, resistance, incline, time, calorie count, respiration rate, other physiological parameters, other exercise parameters, or combinations thereof may be displayed in the display screen of the display device. In some examples, the parameter is sent by the exercise machine and/or sensors to the media content source, and the media content source incorporates the user's parameters into the media content. In other examples, the exercise machine and/or sensors sends the parameter to the display device, where the display device overlays the parameter onto the media content.

At block 610, multiple users are compared in the media content based at least in part on the exercise parameters. For example, the exercise parameters of other users may also be received by the media content or other source, which causes the exercise parameters of the other users to be displayed in the media content. In this example, the exercise parameters of the other users may be displayed with the exercise parameters of the user. Displaying both the user's exercise parameters and the exercise parameters of other users together with the display device also allows those viewing the display device to compare the parameters against one another.

At block 612, the user is compared with an individual in the media content based at least in part on the exercise parameters by displaying a comparison in the media content. In some examples, the comparison is accomplished by displaying the exercise parameter of the user in the media content with exercise parameters of the individuals in the media content. For example, the times it takes for the cyclists in a race to reach a milepost may be displayed in the media content along with the time that it takes the user to reach the same milepost virtually through the fitness program.

Figure 7:
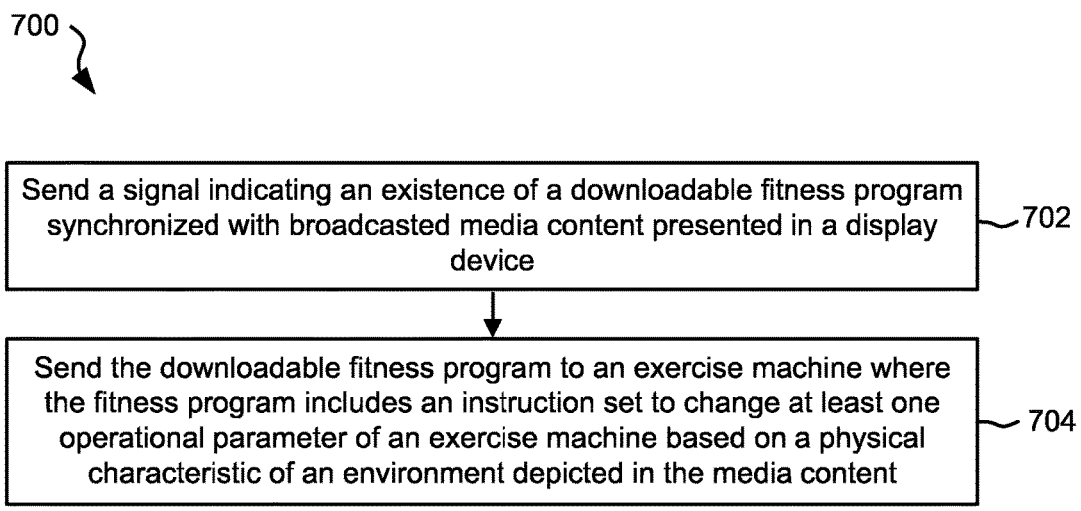
FIG. 7 illustrates a block diagram of an example of a method for providing interaction with broadcasted content in accordance with the present disclosure.

FIG. 7 is a flow diagram illustrating one embodiment of a method 700 for providing interaction with broadcasted content. In this example, the method 700 includes sending 702 a signal indicating an existence of a downloadable fitness program synchronized with broadcasted media content presented in a display device and sending 704 the downloadable fitness program to an exercise machine where the fitness program includes an instruction set to change at least one operational parameter of an exercise machine based on a physical characteristic of an environment depicted in the media content. This method 700 may be implemented with a system 100, 300 in FIGS. 1 and/or 3. In other examples, method 700 may be performed generally by the environment shown in FIG. 1.

At block 702, a signal indicating an existence of a downloadable fitness program is sent. This fitness program is synchronized with broadcasted media content presented in a display device. This signal may be sent from the source of the media content or from another source. In some examples, the signal is sent to the display device, which relays the signal to nearby exercise machines. In other examples, the signal may cause a message about the fitness program to be displayed in the display device. In yet other examples, the signal is sent to a mobile device or any other appropriate device that may communicate to the user the existence of the fitness program.

At block 704, the downloadable fitness program is sent to an exercise machine. In some examples, the user may request the fitness program in response to receiving the signal about the existence of the fitness program. The fitness programs may be sent over the internet, over a television network, over another type of channel, or combinations thereof. The fitness program may control at least one aspect of the exercise machine based on changes to the physical characteristics of the environment depicted in the media content.

Figure 8:
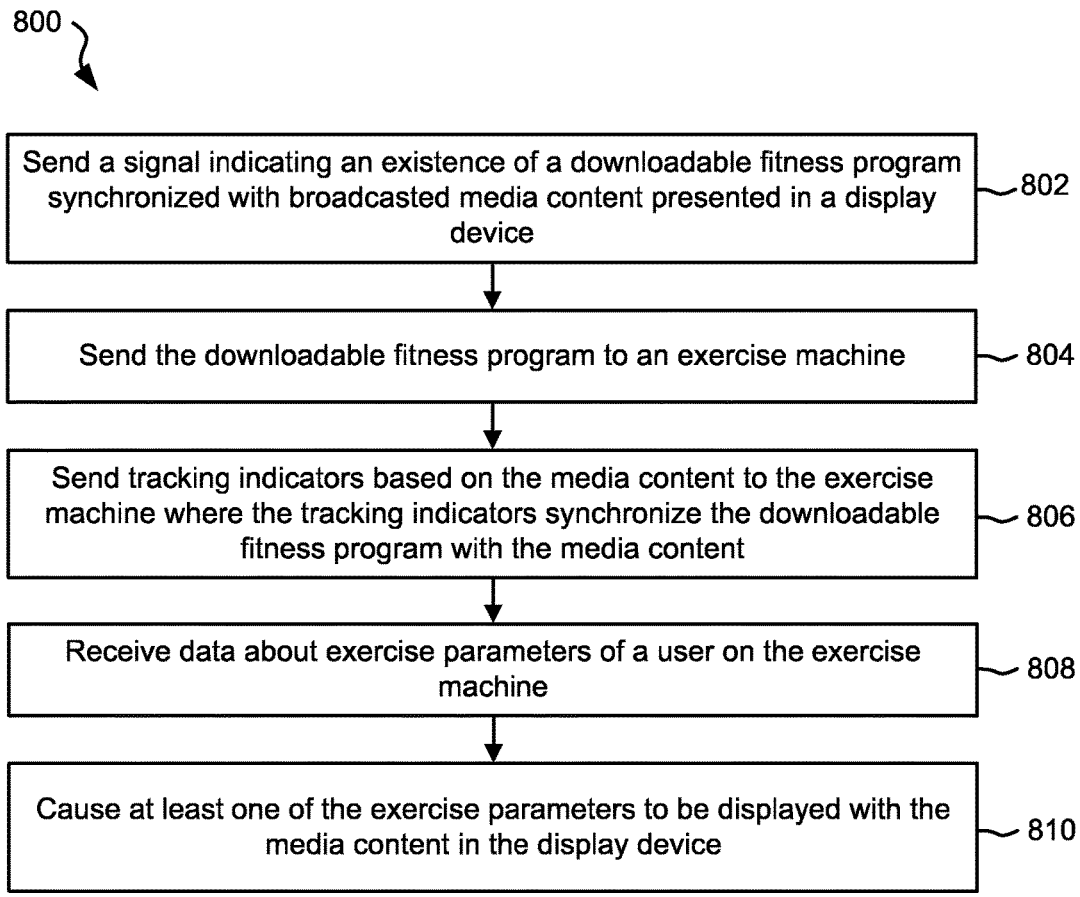
FIG. 8 illustrates a block diagram of an example of a method for providing interaction with broadcasted content in accordance with the present disclosure.

FIG. 8 is a flow diagram illustrating one embodiment of a method 800 for providing interaction with broadcasted content. In this example, the method 800 includes sending 802 a signal indicating an existence of a downloadable fitness program synchronized with broadcasted media content presented in a display device, sending 804 the downloadable fitness program to an exercise machine, sending 806 synchronization indicators based on the media content to the exercise machine where the synchronization indicators synchronize the downloadable fitness program with the media content, receive 808 data about exercise parameters of a user on the exercise machine, and causing 810 at least one of the exercise parameters to be displayed with the media content in the display device. This method 800 may be implemented with a system 100, 300 in FIGS. 1 and/or 3. In other examples, method 800 may be performed generally by the environment shown in FIG. 1.

At block 806, synchronization indicators are sent based on the media content to the exercise machine where the synchronization indicators synchronize the downloadable fitness program with the media content. These synchronization indicators may be periodic signals from which the exercise machine can pace the fitness program. In other examples, these synchronization indicators can be sent at times when the media content changes a parameter of the exercise machine.

At block 808, data about the exercise parameters is the user is received. At block 810, at least one of the exercise parameters is caused to be displayed with the media content in the display device. This exercise parameter may be displayed with the exercise parameters of the other using the fitness program and/or individuals depicted in the media content.

Figure 9:
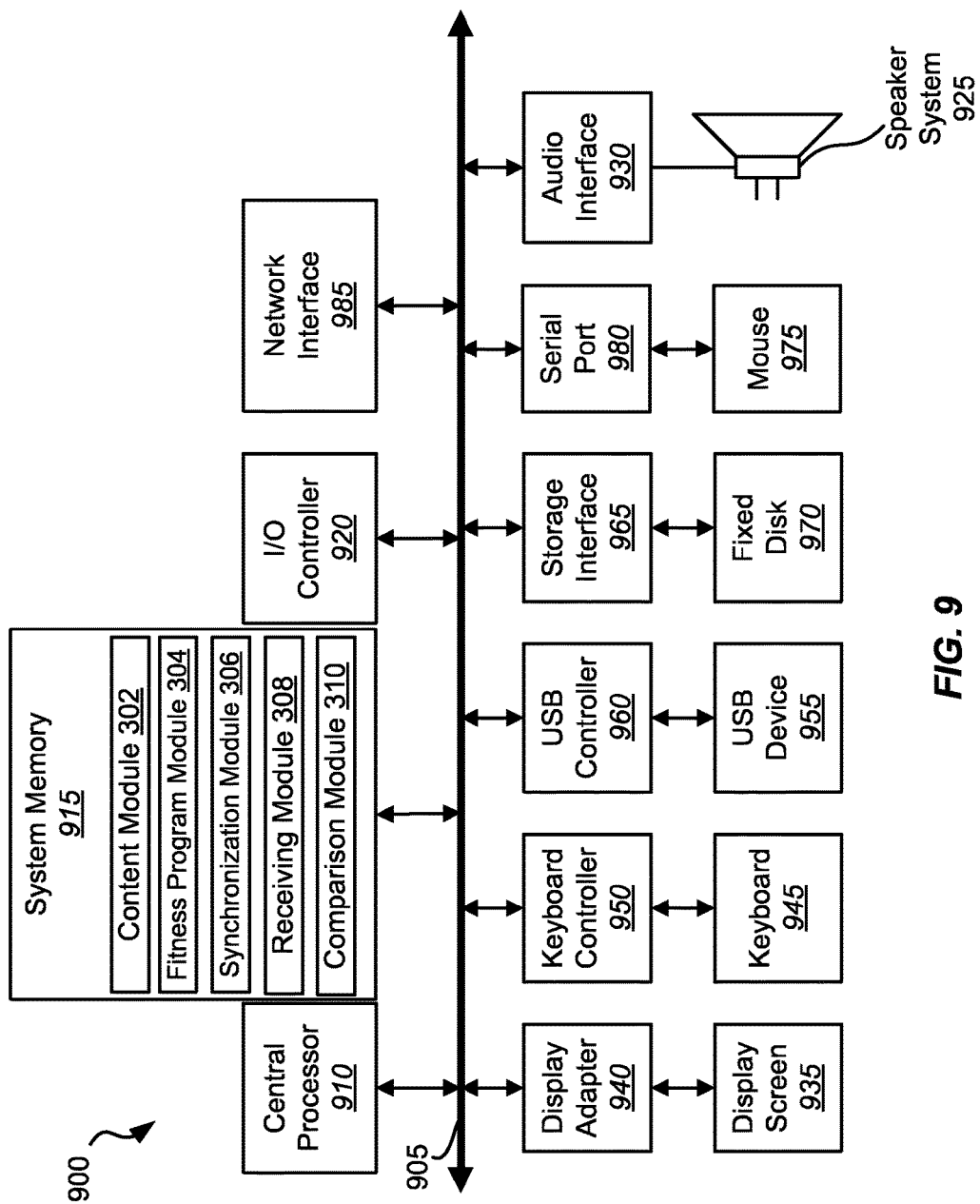
FIG. 9 illustrates a block diagram of an example of a system for interacting with broadcasted content in accordance with the present disclosure.

FIG. 9 depicts a block diagram of a controller 900 suitable for implementing the present systems and methods. The controller 900 may be an example of a controller used to operate the system 100 in FIG. 1 and/or the system in FIG. 4. In one configuration, controller 900 includes a bus 905 which interconnects major subsystems of controller 900, such as a central processor 910, a system memory 915 (typically RAM, but which may also include ROM, flash RAM, or the like), an input/output controller 920, an external audio device, such as a speaker system 925 through an audio output interface 930, an external device, such as a display screen 935 through display adapter 940, an input device 945 (e.g., remote control device interfaced with an input controller 950), multiple USB devices 965 (interfaced with a USB controller 970), one or more cellular radios 990, and a storage interface 980. Also included are at least one sensor 955 connected to bus 905 through a sensor controller 960 and a network interface 985 (coupled directly to bus 905).

Bus 905 allows data communication between central processor 910 and system memory 915, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, a content module 302, a fitness program module 304, a synchronization module 306, a receiving module 308, and a comparison module 310 may be used to implement the present systems and methods may be stored within the system memory 915. These modules may be an example of the modules illustrated in FIG. 4. Applications resident with controller 900 are generally stored on and accessed through a non-transitory computer readable medium, such as a hard disk drive (e.g., fixed disk 975) or other storage medium. Additionally, applications can be in the form of electronic signals modulated in accordance with the application and data communication technology when accessed through network interface 985.

Storage interface 980, as with the other storage interfaces of controller 900, can connect to a standard computer readable medium for storage and/or retrieval of information, such as a fixed disk drive 975. Fixed disk drive 975 may be a part of controller 900 or may be separate and accessed through other interface systems. Network interface 985 may provide a direct connection to a remote server through a direct network link to the Internet via a POP (point of presence). Network interface 985 may provide this connection using wireless techniques, including digital cellular telephone connection, Cellular Digital Packet Data (CDPD) connection, digital satellite data connection, or the like. In some embodiments, one or more sensors connect to controller 900 wirelessly through network interface 985. In one configuration, the cellular radio 990 may include a receiver and transmitter to wirelessly receive and transmit communications through, for example, a cellular network.

Many other devices or subsystems (not shown) may be connected in a similar manner (e.g., entertainment system, computing device, remote cameras, wireless key fob, wall mounted user interface device, cell radio module, battery, alarm siren, door lock, lighting system, thermostat, home appliance monitor, utility equipment monitor, and so on). Conversely, all of the devices shown in FIG. 9 need not be present to practice the present systems and methods. The devices and subsystems can be interconnected in different ways from that shown in FIG. 9. The aspect of some operations of a system such as that shown in FIG. 9 are readily known in the art and are not discussed in detail in this application. Code to implement the present disclosure can be stored in a non-transitory computer-readable medium such as one or more of system memory 915 or fixed disk 975. The operating system provided on controller 900 may be iOS®, ANDROID®, MS-DOS®, MS-WINDOWS®, OS/2®, UNIX®, LINUX®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. But, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best use the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

INDUSTRIAL APPLICABILITY

In general, the invention disclosed herein may provide a user with an opportunity to interact with media content. The television station or other sources may provide a fitness program that is associated with the media content and is made available for the user to download. This fitness program can be synchronized with the media content and may help the user appreciate at least one aspect of information presented in the media content. For example, if the media content is a cycling competition, the fitness program may cause the exercise machine to simulate at least one aspect of the race course. For example, the incline of the exercise machine may be changed to simulate the steepness of the race course, the resistance of the exercise machine may be changed to reflect a wind resistance of the race course, frequent changes in the incline angle of the exercise machine may simulate the ruggedness of the race course's terrain, and so forth.

The principles of the present invention may include media content that includes a documentary program. In this example, the incline of the exercise machine may simulate the steepness of the mountain, the resistance of the exercise machine may simulate a difficulty of the traveling through snow deposited in the mountain, frequent changes in the incline angle of the exercise machine may simulate the ruggedness of the mountain, and so forth. Further, the principles of the present invention may include fictional content, such as movies, sitcoms, or other entertainment based programs. In this example, the speed of the exercise machine may simulate the speed of a character, machine or animal in the fictional content, the resistance of the exercise machine may simulate a difficulty of a condition of a character in the fictional content, the incline angle of the exercise machine may simulate the route taken by a character in the fictional content, and so forth.

The signal indicating the existence of the fitness program may be sent from the television network or another broadcasting network. In this example, the signal may be broadcasted in the media content or independently of the media content. In some examples, the signal causes a message to be displayed in the display device about the fitness program. In other examples, the signal is sent to the exercise machine, a mobile device, or another device associated with the user through the display device. In other examples, the signal is sent directly to the exercise machine, mobile device, or other device associated with the user or through another type of device. In some examples, the signal causes an email, text message, or another type of message to be sent to a device associated with the user. In yet another example, the signal causes a posting on a website that indicates the existence of the fitness program.

In other examples, a third party may contract with the television networks to create a fitness program for their media content. In this example, the third party may use the television network to broadcast the signal and/or the fitness program. In other examples, the third party uses an independent channel to make either the signal or the fitness program available to the user.

In one example, the system includes a display screen, a content module, a fitness program module, a synchronization module, a receiving module, and a comparison module. The content module may include any appropriate mechanism for delivering media content to the display device. In some examples, the media content is delivered through a streaming mechanism. In some examples, the media content includes a portion of a television series, a television special, a movie, a sitcom, an education program, a live event, a short video clip, another type of media content, or combinations thereof. The media content may be spectator content.

The fitness program module may include any appropriate instruction set that may be used to control the exercise machine. This instruction set may be downloaded from an online source, sent from the media content source, sent from a third party, or available from another mechanism. The fitness program may be configured to operate any appropriate type of exercise machine, such as a treadmill, an elliptical, a stationary bike, a stepper machine, a skiing machine, a rowing machine, another type of machine, or combinations thereof. The fitness program may control the exercise machine's incline, resistance, speed, side to side tilt, height, other parameters of the exercise machine, or combinations thereof.

In some aspects of the invention, the fitness program module includes an instruction set that causes at least one operational parameter of the exercise machine to change based on at least one physical characteristic of a physical environment depicted in the media content. For example, if the slope of a road or race track changes relative to horizontal, the incline of the exercise machine may also change.

The synchronization module may include any appropriate mechanism for syncing the fitness program with the media content. In some situations, the exercise machine is caused to change parameters in response to different conditions being depicted in the media content. For example, as the slope of the route depicted in the media content changes, so may the incline of the exercise machine. In other examples, the media content may depict a route that competitors in the media content are using, and the fitness program may cause the exercise machine to mimic the route based on the user's performance and not necessarily the performance of the competitors. In this situation, the user may not be synced with the competitors, but the user may be synced with a map of the route.

In some cases, synchronization indicators may be sent from the source of the media content, the source of the fitness program, another source, or combinations thereof. In these circumstances, the synchronization indicators provide details about where the fitness program may be based on the media content. For example, the synchronization indicators may be sent at periodic intervals, which enables the fitness program to determine the pace at which it should control the exercise machine. In other examples, the synchronization indicators may be sent from the media content to indicate when a change to the exercise machine's operating parameters should be made. For example, when the media content depicts weather changes to a competitor depicted in the media content, such as a gust of wind, the media content source may send a synchronization indicator to indicate a new resistance level at which the exercise machine should be set for synchronizing the experience of the competitor in the media content with the experience of the user.

The receiving module may include any appropriate mechanism for receiving input from the exercise machines. For example, the receiving module may be capable of receiving a signal from the exercise machine that conveys at least one parameter of the user's workout. In some examples, the parameters of the workout that may be sent to the receiving module include a distance, a time taken to achieve a milestone, a physiological parameter, another condition, or combinations thereof.

The comparison module may include any appropriate mechanism for comparing the parameters of the user's workout with exercise parameters of other users, individuals depicted in the media content, animals or machines depicted in the media content, or combinations thereof. For example, the time that a user takes to virtually reach a certain checkpoint in a race course may be compared to the actual time that it took the cyclists depicted in the media content. In this example, the times of selected cyclists may appear in the display screen and the times of the user may appear next to their displayed times. By having the cyclists' times displayed next to the user's time, the user can compare his performance against the cyclists. In other examples, the user's time may be displayed adjacent to other users also using the fitness program. In other examples, the speed of an animal depicted in the media content may be displayed next to the user's speed for comparison.

The exercise machine may include a receiver, an input mechanism, a fitness program downloader, a fitness program executer, and a synchronization tracker. The receiver may include any appropriate mechanism to receive an appropriate signal indicating that a fitness program is associated with the media content exists. In some examples, the receiver receives the signal from the television displaying the media content, the source of the media content, a source of a fitness program, a third party, another source, or combinations thereof.

The input mechanism may include any appropriate mechanism for the user to select an option to obtain and/or retrieve the fitness program. In some situations, the receiver may cause a message to be displayed in a console of the exercise machine or otherwise communicate the message to the user that a fitness program is available. In this situation, the user may use the input mechanism to select an option to download the fitness program with the fitness program downloader. In some examples, the user can use the input mechanism to select an appropriate version of the fitness program, such as a fitness program specific for a treadmill. In other examples, the exercise machine automatically determines the appropriate version of the fitness program based on the exercise machine's type. In yet other examples, the fitness program is written in this format that allows the fitness program to be executed on multiple types of exercise machines. For example, a single fitness program may be executable on various kinds of treadmills, elliptical trainers, and stationary bikes.

The fitness program executer may include any appropriate type of mechanism to execute the fitness program. This executer may be in communication with actuators that move the exercise platform, change the machine's resistance, change the machine's height, change the machine's side to side tilt, change a motor speed, change another parameter of the exercise machine, or combinations thereof.

The synchronization tracker may include any appropriate type of mechanism to synchronize the fitness program with the media content. For example, the synchronization tracker may receive periodic signals associated with the media content that the synchronization tracker can use to establish a pace of the exercise machine. In other examples, the synchronization tracker can receive inputs from the media content source or other source as to when to make certain changes. In this example, the synchronization tracker may rely on signals from the media content source or other source to make all changes to the exercise machine. But, in other examples the synchronization tracker may rely on these signals to make some changes while relying on other indicators downloaded in the fitness program.

A method may include broadcasting media content to a display, associating a fitness program to the media content with synchronization indicators to synchronize the fitness program with the media content, and controlling an operational parameter of an exercise machine based on physical characteristics of an environment depicted in the media content. The media content may include live events, streamed content, fictional content, documentary content, other types of content, or combinations thereof. In an example, the media content is broadcasted from a television station/network. The display device may be a television, a computer screen, a laptop, a mobile device, a phone, an electronic tablet, another type of display device, or combinations thereof.

The fitness program may be sent at the same time as the media content. In other examples, the fitness program is available for download over the internet or another type of network. The media content may include synchronization indicators that synchronize the fitness program with the media content.

The physical characteristic of an environment may be depicted in the media content. For example, the resistance, incline, speed, height, side to side tilt, or another operational parameter of the exercise machine may change as a physical characteristic in the environment depicted in the media content changes. For example, if a cyclist depicted in the media content is depicted as starting to bike through a sandy portion of a trail, the resistance on an exercise bike may increase. Further, the resistance on the exercise bike may be reduced when the cyclist exits the sandy portion of the trail.

In other examples, the method may include broadcasting media content to a display, associating a fitness program to the media content with synchronization indicators to synchronize the fitness program with the media content, control an operational parameter of an exercise machine based on physical characteristics of an environment depicted in the media content, receive data about exercise parameters of a user on the exercise machine, cause at least one of the exercise parameters to be displayed with the media content in the display device, and compare multiple users based at least in part on the exercise parameters in the media content.

The data may include an incline, a resistance, a speed, a physiological condition, another exercise parameter or combinations thereof. The data may be collected by a sensor incorporated into the exercise machine. In other examples, this data is collected by sensors carried or worn by the user.

The exercise parameters may be caused to be displayed with the media content in the display device. For example, the user's speed, resistance, incline, time, calorie count, respiration rate, other physiological parameters, other exercise parameters, or combinations thereof may be displayed in the display screen of the display device. In some examples, the parameter is sent by the exercise machine and/or sensors to the media content source, and the media content source incorporates the user's parameters into the media content. In other examples, the exercise machine and/or sensors sends the parameter to the display device, where the display device overlays the parameter onto the media content.

The exercise parameters of other users may also be received by the media content or other source, which causes the exercise parameters of the other users to be displayed in the media content. In this example, the exercise parameters of the other users may be displayed with the exercise parameters of the user. Displaying both the user's exercise parameters and the exercise parameters of other users together with the display device also allows those viewing the display device to compare the parameters against one another.

In some examples, the comparison is accomplished by displaying the exercise parameter of the user in the media content with exercise parameters of the individuals in the media content. For example, the times it takes for the cyclists in a race to reach a milepost may be displayed in the media content along with the time that it takes the user to reach the same milepost virtually through the fitness program.

In yet other examples, the method may include sending a signal indicating an existence of a downloadable fitness program synchronized with broadcasted media content presented in a display device and sending the downloadable fitness program to an exercise machine where the fitness program includes an instruction set to change at least one operational parameter of an exercise machine based on a physical characteristic of an environment depicted in the media content.

The fitness program is synchronized with broadcasted media content presented in a display device. This signal may be sent from the source of the media content or from another source. In some examples, the signal is sent to the display device, which relays the signal to nearby exercise machines. In other examples, the signal may cause a message about the fitness program to be displayed in the display device. In yet other examples, the signal is sent to a mobile device or any other appropriate device that may communicate to the user the existence of the fitness program.

The user may request the fitness program in response to receiving the signal about the existence of the fitness program. The fitness programs may be sent over the internet, over a television network, over another type of channel, or combinations thereof. The fitness program may control at least one aspect of the exercise machine based on changes to the physical characteristics of the environment depicted in the media content.

Additionally, another method may include sending a signal indicating an existence of a downloadable fitness program synchronized with broadcasted media content presented in a display device, sending the downloadable fitness program to an exercise machine, sending synchronization indicators based on the media content to the exercise machine where the synchronization indicators synchronize the downloadable fitness program with the media content, receive data about exercise parameters of a user on the exercise machine, and cause at least one of the exercise parameters to be displayed with the media content in the display device.

The synchronization indicators may be periodic signals from which the exercise machine can pace the fitness program. In other examples, these synchronization indicators can be sent at times when the media content changes where the fitness program is to cause a change to a parameter of the exercise machine. The exercise parameter may be displayed with the exercise parameters of the other using the fitness program and/or individuals depicted in the media content.

What is claimed is:

1. A method for providing interaction with media content, comprising:
   broadcasting media content to a display device, wherein the media content includes a competitor or an actor without communication with an audience viewing the media content;
   while broadcasting media content to the display device, associating a downloadable fitness program with the media content with synchronization indicators to synchronize the downloadable fitness program with the media content; and
   controlling an operational parameter of an exercise machine based on physical characteristics of an environment depicted in the media content.

2. The method of claim 1, wherein the media content depicts a live competition between non-users.

3. The method of claim 1, further comprising receiving data about exercise parameters of a user on the exercise machine.

4. The method of claim 3, further comprising causing at least one of the exercise parameters to be displayed with the media content in the display device.

5. The method of claim 3, further comprising comparing multiple users based at least in part on the exercise parameters in the media content.

6. The method of claim 3, further comprising comparing the user with an individual in the media content based at least in part on the exercise parameters by displaying a comparison in the media content.

7. The method of claim 1, wherein the downloadable fitness program includes an instruction set to adjust a resistance of the exercise machine, adjust an incline of the exercise machine, adjust a speed of the exercise machine, or combinations thereof.

8. The method of claim 1, wherein the media content is a scheduled fitness program.

9. The method of claim 1, wherein broadcasting media content to the display device includes streaming the media content to the display device.

10. The method of claim 1, wherein the media content is a documentary.

11. The method of claim 1, wherein the media content is a fictional film.

12. The method of claim 1, wherein associating the downloadable fitness program to the media content with the synchronization indicators to synchronize the downloadable fitness program with the media content includes broadcasting the synchronization indicators with the media content.

13. A system for providing interaction with media content, comprising:
a memory and processor, the memory comprising program instructions that cause the processor to:
broadcast media content to a display device, wherein the media content includes a competitor or an actor unaware of an audience viewing the media content;
while broadcasting media content to the display device, attach a fitness program to the media content that controls at least one operational parameter of an exercise machine based on a physical characteristic of an environment depicted in the media content; and
synchronize the fitness program with the media content.

14. The system of claim 13, wherein the programmed instructions further cause the processor to receive at least one exercise parameter of a user.

15. The system of claim 13, wherein the programmed instructions further cause the processor to:
compare a user with an individual depicted in the media content; and
display a comparison in the display device with the media content.

16. The system of claim 13, wherein the media content depicts a live competition.

17. The system of claim 13, wherein the media content is a scheduled fitness program.

18. The system of claim 13, wherein the programmed instructions further cause the processor to synchronize the fitness program with the media content by providing multiple synchronization indicators with the media content.

19. An exercise machine, comprising:
a receiver to receive a signal indicating an existence of a downloadable fitness program, the downloadable fitness program being synchronized with media content while the media content is presented in a display device where competitors or actors of the media content do not interact with an audience viewing the media content;
an input mechanism to receive input to download the downloadable fitness program; and
a processor to execute the downloadable fitness program while the media content is presented in the display device;
wherein the downloadable fitness program includes an instruction set that changes at least one operational parameter of the exercise machine based on a physical characteristic of an environment depicted in the media content.

20. The exercise machine of claim 19, wherein the at least one operational parameter includes one or more of adjusting a resistance of the exercise machine, adjusting an incline of the exercise machine, and adjusting a speed of the exercise machine.

* * * * *